(12) United States Patent
Santin et al.

(10) Patent No.: US 9,474,642 B2
(45) Date of Patent: Oct. 25, 2016

(54) NASAL CONGESTION AND OBSTRUCTION RELIEF AND BREATHING ASSIST DEVICES

(75) Inventors: Ernest Santin, Beverly, MA (US); Louise S. MacDonald, Beverly, MA (US)

(73) Assignee: SANOSTEC CORP, Beverly Farms, MA (US)

( * ) Notice: Subject to any disclaimer, the term of this patent is extended or adjusted under 35 U.S.C. 154(b) by 2616 days.

(21) Appl. No.: 10/842,220

(22) Filed: May 10, 2004

(65) Prior Publication Data

US 2005/0021073 A1    Jan. 27, 2005

Related U.S. Application Data

(63) Continuation-in-part of application No. 10/434,669, filed on May 9, 2003, now Pat. No. 7,390,331, which is a continuation-in-part of application No. 09/862,966, filed on May 22, 2001, now Pat. No. 6,562,057.

(51) Int. Cl.
   *A61F 5/08*    (2006.01)

(52) U.S. Cl.
   CPC ..................................... *A61F 5/08* (2013.01)

(58) Field of Classification Search
   CPC .............. A61F 5/01; A61F 5/08; A61F 5/56; A61M 29/00
   USPC ....... 606/196, 198, 199; 128/204.12, 200.24, 128/200.26
   See application file for complete search history.

(56) References Cited

U.S. PATENT DOCUMENTS

| | | | |
|---|---|---|---|
| 682,123 A | 9/1901 | Wilson | |
| 753,133 A | 2/1904 | Gamble | |
| 810,617 A | 1/1906 | Carence | |
| 878,223 A | 2/1908 | Meisselbach | |
| 888,869 A | 5/1908 | Clark | |
| 1,034,123 A | 7/1912 | Knowlson | |

(Continued)

FOREIGN PATENT DOCUMENTS

| DE | 199 03 782 C1 | 7/2000 |
|---|---|---|
| DE | 10 2005 037843 A1 | 2/2007 |

(Continued)

OTHER PUBLICATIONS

The International Search Report and The Written Opinion (PCT/US04/14501).

(Continued)

*Primary Examiner* — Victor Nguyen
(74) *Attorney, Agent, or Firm* — Nutter McClennen & Fish LLP

(57) ABSTRACT

A nasal breathing assist device includes one or two open-ended tubular elements each extending along a central tube axis between a relatively large first end and a relatively small second end, and at least one non-resilient tab extends from the first end toward the second end of the tubular element. In embodiments with two tubular elements, a coupler element extends between the first ends of the tubular elements. Each tubular element may further include a liner-shaped filter having a liner portion extending along a central axis between a relatively large end and a relatively small end, and a filter medium spanning at least one of the relatively large end and the relatively small end. The filter is adapted to snap-fit in the tubular element. The tubular element may further include at least one stiffening element affixed to the tubular element.

16 Claims, 16 Drawing Sheets

(56) References Cited

U.S. PATENT DOCUMENTS

| | | | |
|---|---|---|---|
| 1,077,574 A | 11/1913 | Woodward | |
| 1,087,186 A | 2/1914 | Scholfield | |
| 1,139,357 A | 5/1915 | Garske | |
| 1,160,797 A | 11/1915 | Wallin | |
| 1,256,188 A | 2/1918 | Wilson | |
| 1,311,461 A | 7/1919 | Reynard | |
| 1,322,375 A | 11/1919 | Un | |
| 1,481,581 A | 2/1924 | Woodward | |
| 1,839,606 A | 1/1932 | Simmons | |
| 2,010,485 A | 8/1935 | Heath | |
| 2,151,227 A | 3/1939 | Pawelek | |
| 2,237,954 A | 4/1941 | Wilson | |
| 2,264,153 A | 11/1941 | Rowe | |
| 2,277,390 A | 3/1942 | Crespo | |
| 2,335,936 A * | 12/1943 | Hanlon | 606/199 |
| 2,433,565 A | 12/1947 | Korman | |
| 2,515,756 A | 7/1950 | Bove | |
| 2,569,743 A | 10/1951 | Carlock | |
| 2,663,297 A | 12/1953 | Turnberg | |
| 2,672,138 A | 3/1954 | Carlock | |
| 3,424,152 A | 1/1969 | Kuhlman | |
| 3,463,149 A | 8/1969 | Albu | |
| 3,710,799 A | 1/1973 | Caballero et al. | |
| 3,742,943 A | 7/1973 | Malmin | |
| 3,747,597 A * | 7/1973 | Olivera | 128/206.11 |
| 3,802,426 A | 4/1974 | Sakamoto | |
| 4,105,035 A | 8/1978 | Rella | |
| 4,120,299 A | 10/1978 | Russo | |
| 4,221,217 A * | 9/1980 | Amezcua | 128/206.11 |
| 4,267,831 A | 5/1981 | Aguilar | |
| 4,414,977 A | 11/1983 | Rezakhany | |
| D279,708 S | 7/1985 | Child | |
| 4,573,461 A | 3/1986 | Lake | |
| 4,592,357 A | 6/1986 | Ersek | |
| 5,417,205 A | 5/1995 | Wang et al. | |
| 5,425,359 A | 6/1995 | Liou et al. | |
| 5,479,944 A | 1/1996 | Petruson | |
| 5,533,503 A | 7/1996 | Doubek et al. | |
| 5,601,594 A | 2/1997 | Best | |
| 5,603,317 A | 2/1997 | Farmer | |
| 5,665,104 A | 9/1997 | Lee | |
| 5,725,547 A | 3/1998 | Chuter | |
| 5,775,335 A | 7/1998 | Seal | |
| 5,816,241 A | 10/1998 | Cook | |
| 5,853,422 A | 12/1998 | Huebsch et al. | |
| 5,895,409 A | 4/1999 | Mehdizadeh | |
| 5,925,060 A | 7/1999 | Forber | |
| 5,931,852 A * | 8/1999 | Brennan | 606/199 |
| 5,941,244 A | 8/1999 | Yamazaki et al. | |
| 6,004,342 A * | 12/1999 | Filis | 606/199 |
| 6,017,315 A * | 1/2000 | Starr et al. | 600/538 |
| 6,024,756 A | 2/2000 | Huebsch et al. | |
| 6,106,541 A * | 8/2000 | Hurbis | 606/199 |
| 6,386,197 B1 | 5/2002 | Miller | |
| 6,416,540 B1 | 7/2002 | Mathur | |
| 6,561,188 B1 | 5/2003 | Ellis | |
| 6,562,057 B2 | 5/2003 | Santin | |
| 6,602,282 B1 | 8/2003 | Yan | |
| 6,863,066 B2 | 3/2005 | Ogle | |
| 6,893,450 B2 | 5/2005 | Foster | |
| 6,978,781 B1 | 12/2005 | Jordan | |
| 7,331,989 B2 | 2/2008 | Houston et al. | |
| 7,390,331 B2 | 6/2008 | Santin et al. | |
| 7,582,111 B2 | 9/2009 | Krolik et al. | |
| 7,637,939 B2 | 12/2009 | Tischler | |
| 7,856,979 B2 | 12/2010 | Doshi et al. | |
| 8,262,688 B2 | 9/2012 | Santin et al. | |
| 8,403,954 B2 | 3/2013 | Santin et al. | |
| 9,242,080 B2 | 1/2016 | MacDonald | |
| 2003/0079749 A1 | 5/2003 | Strickland et al. | |
| 2003/0106555 A1 | 6/2003 | Tovey | |
| 2003/0195552 A1 | 10/2003 | Santin | |
| 2004/0147954 A1 | 7/2004 | Wood | |
| 2005/0021073 A1 | 1/2005 | Santin et al. | |
| 2006/0085027 A1 | 4/2006 | Santin et al. | |
| 2006/0150978 A1 | 7/2006 | Doshi et al. | |
| 2006/0259064 A1 | 11/2006 | Maryanka | |
| 2007/0010851 A1 | 1/2007 | Chanduszko et al. | |
| 2007/0066198 A1 | 3/2007 | Rambosek et al. | |
| 2007/0106328 A1 | 5/2007 | Wardle et al. | |
| 2007/0208368 A1 | 9/2007 | Katoh et al. | |
| 2007/0239199 A1 | 10/2007 | Jayaraman | |
| 2008/0183299 A1 | 7/2008 | Monga et al. | |
| 2008/0262531 A1 | 10/2008 | Santin et al. | |
| 2009/0093840 A1 | 4/2009 | MacDonald | |
| 2010/0063532 A1 | 3/2010 | Moore | |
| 2012/0283769 A1 | 11/2012 | Cruise et al. | |
| 2013/0109987 A1 | 5/2013 | Kunis et al. | |
| 2013/0131716 A1 | 5/2013 | Cruise et al. | |
| 2013/0296809 A1 | 11/2013 | Santin et al. | |

FOREIGN PATENT DOCUMENTS

| | | |
|---|---|---|
| GB | 0 210 982 A | 2/1924 |
| GB | 2126101 | 3/1984 |
| JP | 11192251 | 7/1999 |
| JP | 2002-301152 A | 10/2002 |
| WO | WO 2004/026391 | 4/2004 |
| WO | 2004/069110 A1 | 8/2004 |
| WO | 2007/018458 A1 | 2/2007 |

OTHER PUBLICATIONS

European Search Report and Supplementary Search Report, for EP06840036.5, dated Oct. 27, 2009 and Nov. 4, 2009.

Egan, K. et al., "A Novel Intranasal Stent for Functional Rhinoplasty and Nostril Stenosis" Laryngoscope 115(5):903-09 (May 2005).

International Search Report, for PCT/US04/014501, mailed Nov. 23, 2004.

International Search Report, for PCT/US06/61280, mailed Jul. 11, 2008.

International Search Report, for PCT/US08/078781, mailed Mar. 16, 2009.

Extended European Search Report for Application No. 08835440.2 issued Jun. 26, 2013 (6 Pages).

Japanese Office Action issued Mar. 5, 2013 for Application 2010-528169 (3 Pages).

Japanese Office Action issued Apr. 19, 2016 for Application 2010-528169, Appeal No. 2015-000864 (11 pages).

Indian Office Action for Application No. 3358/CHENP/2008, issued Aug. 26, 2016 (7 pages).

* cited by examiner

NASAL CONGESTION AND OBSTRUCTION RELIEF AND BREATHING ASSIST DEVICES

CROSS-REFERENCE TO RELATED APPLICATIONS

This application is a continuation in part of U.S. patent application Ser. No. 10/434,669, filed May 9, 2003, now U.S. Pat. No. 7,390,331, which is a continuation-in-part of U.S. patent application Ser. No. 09/862,966, filed on May 22, 2001, now U.S. Pat. No. 6,562,057, the disclosures of which are incorporated herein by reference.

FIELD OF THE INVENTION

This invention pertains to methods and devices for nasal congestion and obstruction relief and breathing assist devices, and in particular to methods and devices for improving nasal breathing, treatment of sinus conditions, and reducing snoring.

BACKGROUND OF THE INVENTION

Nasal obstruction is characterized by anatomical conditions including nasal valve collapse, nasal valve obstruction, septal deviation, and medium hypertrophy. These conditions obstruct and restrict nasal airflow causing difficulties in breathing through the nose.

Limited or obstructed nasal airflow reduces the normal ventilation of sinuses. Properly ventilated sinuses allow healthy draining for cleaning of the sinuses. Without proper ventilation, sinuses may not drain properly, which can cause infections in the sinuses. Chronic sinusitis is a condition characterized by long lasting sinus infections, which are caused by obstructed or restricted nasal airflow.

Snoring is a condition characterized by rough, loud, rattling breathing, or aspiratory noise in the throat during sleep or deep coma. The characteristic snoring noise is produced by vibration of the soft palate (the soft tissue in the roof of the mouth near the throat) or vocal chords by inhaled or exhaled air. As the soft palate vibrates, the lips, cheeks, and nostrils may also vibrate, making the snoring louder.

Snoring can be caused by underlying physical or disease conditions that restrict air passages and force the patient to breathe through their mouth with exaggerated force to move air through narrowed nasal passages. Chronic snoring can be the result of obstruction of nasal airways, septal deviation, or obstructed nasal passages. Temporary snoring, or a sudden onset of snoring can be the result of congestion or swollen nasal mucus membranes, as with a cold or hay fever, or a nasal polyp.

Anatomical deformities in the airway such as septal deviation, medium hypertrophy, obstructed nasal valves and nasal valve collapse can diminish the airway size. Fat deposits around the nasal passages, as found in obesity, can make the nasal passages smaller. Poor muscle tone in the muscles of the tongue and throat, or medications and foods (such as alcohol) that relax these muscles also increase snoring.

Snoring can cause relationship problems between partners, and lead to a loss of intimacy and deterioration of relationships. Loss of sleep, or insufficient rest during sleep increases irritability, reduces memory and concentration, and decreases work performance.

A number of methods and devices have been developed to reduce or eliminate snoring. Some devices are external to the patient and include buzzer systems and alarms that wake the patient. Special pillows, neck collars, chin braces and head straps have also been tested in an effort to control snoring. When nasal obstruction, chronic sinusitis, or snoring is caused by serious deformity, surgery has been performed to remove anatomical obstructions, such as removing tonsils, or correcting medium hypertrophy, or septal deviation. For snoring, occasionally a procedure called UPPP (Uvulopalatopharyngoplasty) is recommended. This procedure acts like an internal facelift, tightening loose tissue. However, the success rate is only 50%. Laser surgery to correct airway defects is also available in some cases.

Other remedies for chronic sinusitis or snoring include prescription antibiotics, herbal and homeopathic rinses, sprays or potions, and OTC medications such as decongestants and antihistamines. Diet and lifestyle changes may reduce snoring to some degree. Nasal valve collapse is a soft tissue condition that is inoperable. Remedies are limited to rigid and metal spring like products. Use of this type of products is limited due to the discomfort or metal taste.

Various devices have been developed for nasal congestion and obstruction relief and sinus or snore relief that keep the mouth, or nasal passages open, or the tongue depressed. Devices marketed for snoring through the dental channel can be expensive custom-fit, or inexpensive over the counter mouth pieces. Adhesive nasal strips, which are applied externally to either side of the nose, have been developed. While these strips may dilate the nasal passages to small degree, they do not work well in patients with significant anatomical deformities or obstructions in the nose. Air masks that force pressurized air into the mouth and lungs are available. These devices can be cumbersome, unsightly, painful, or expensive, and the patient may abandon these approaches in short time.

Sinusitis is another common nasal disease. Sinusitis is inflammation or infection of the mucous membranes that line the inside of the nose and sinuses. It can be caused by bacteria, viruses, and possibly by allergies. Chronic sinusitis is a prolonged sinus infection which generally last longer than 12 weeks. Chronic sinusitis is difficult to treat because it responds slowly to medications. Conventional treatment for chronic sinusitis includes oral antibiotics, nasal spray, and sinus surgery. These treatments generally cannot get directly to the source of the problem, or may cause side effect, for example, frequently using nasal spray may worsen the symptom.

SUMMARY OF THE INVENTION

The object of the present invention is to reduce snoring by increasing the airflow through the nasal passages. It is a further object to provide devices that relieve nasal congestion and obstruction to improve nasal breathing by increasing airflow through the nasal passages during sleep. It is another object of the present invention to treat chronic sinusitis.

One aspect of the invention provides "dual tube" nasal breathing assist devices having a pair of open-ended tubular elements connected together by a coupler element. The tubular elements are preferably conic-frustum shaped along a tube axis, having a relatively large first end and a relatively smaller second end, and tapering from the first end to the second end along the tube axis. In some embodiments, each tubular element may have passageways extending through the tubular elements transverse to the tube axis. These passageways may be elongated, and extend at least in part in the direction of the tube axes.

The coupler element maintains the tubular element in a generally parallel relationship to each other in a common plane and in a spaced-apart relation which corresponds generally to the separation between the user's nostrils.

In one embodiment, the coupler element is a resilient, nominally curved strut lying in a plane substantially perpendicular to the tube axes, permitting relative angular motion of the tube elements about an axis perpendicular to the tube axes.

In an alternate embodiment, the coupler element is a resilient, nominally curved strut lying in a plane substantially parallel to the tube axes, permitting relative angular motion of the tube element about an axis parallel to the tube axes.

In another embodiment of the invention, a "single tube" nasal breathing assist device is a single, open-ended, resilient tubular element, adapted for insertion into a user's nostril. The tubular element is conic-frustum shaped, having a relatively large diameter first end and a relatively smaller diameter second end, and a taper extending from the first end to the second end along a tube axis. The tubular element may have passageways extending through the tubular element transverse to the tube axis. In one form, these passageways may be elongated. The single tube may be used in a user's nostril, and if desired, together with another single tube in the user's other nostril. In this form, the tubes are not coupled to each other.

In some forms of both the single tube or dual tube embodiments of the invention, the tubular elements have a tab extending from the first (i.e. relatively large) end which extends substantially parallel to the tube axis and is elongated in the direction of the tube axis. In yet another embodiment, each tube element has a tab support extending radially from the first end in a direction substantially perpendicular to the tube axis. At least one tab extends from the tab support, and is elongated in the direction of the tube axis. The tabs may be resiliently deformable, so as to permit elastic deformation in use, providing a frictional holding force when engaging the nose. Alternatively, the tabs may be non-resiliently deformable, permitting inelastic deformation, so that a user can "pinch" the tabs so that they capture and hold the nose. The non-resilient tabs are preferably made with a stiffening material embedded in, affixed to, or of plastic or metal, for example, copper, aluminum, but may be made of other materials that may be non-resiliently deformed. The tab preferably includes at least one relatively small protrusion extending from a distal end of the tab. The distal end is distal from the first end of the tubular element. The relatively small protrusion may also extend from the outer surface of the tubular element opposing the distal end of the tab. The tab and the protrusion help to prevent the device from slipping out of a user's nose.

In another preferred embodiment, the tab has an inner surface, which faces the tubular element and is at least partially coated with adhesive. In use, after the device is inserted into a user's nostrils, the tab and the outer surface of the tubular element hold the lateral wall of the user's nose, and the adhesive coating increases the friction between the tab and the outer surface of the user's nose, and make the tab to stick to the outer surface of the user's nose, thus increasing the stability of the device within the user's nose.

The tubular element includes, preferably at its large end, an open-faced channel extending about its tube axis. The device further includes a filter having a peripheral frame contoured to snap-fit in the open-faced channel. The filter includes a filter medium, preferably but not necessarily, a composite filter of manmade or natural materials, i.e. paper, metal or plastic with or without a coating of absorbent materials, spanning the peripheral frame. In an alternate embodiment, at least one relative small protrusion extends from an inner surface of the channel. The filter is adapted to snap-fit over the protrusion into the channel and is retained by the protrusion, so that the filter cannot slip out from the channel when the device is in use. In a preferred embodiment, the protrusion extends throughout an inner circumference of the channel. In another preferred form, the filter includes a liner portion extending along a central axis between a relatively large end and a relatively small end, and a filter medium spanning at least one of the relatively large end and the relatively small end. In an alternative form, the liner portion and the filter medium are integrally constructed from a sheet or composite of a filter medium.

In another preferred embodiment, the device is embedded or coated with a therapeutic agent or further includes at least one carrier, which may or may not be removable, which may include a medium, for example a metal or plastic mesh, or a surface, adapted to bear a therapeutic agent. The carrier may be a disc, tablet, or a liner that affixes to the inside of the tubular element. These embodiments may include two opposite edges, and can include multi-edged configurations, for example as in a star shape. The tubular element further defines two or more opposing channels on an inner surface of the tubular element. The two or more opposing channels extend in a plane substantially parallel to the central axis and are adapted to receive the two or more opposite edges of said removable or permanently placed carrier. The therapeutic agent may be medications, for example, antibiotics, for treating chronic sinusitis or other nasal diseases.

In a further preferred embodiment, the tubular element includes at least one substantially annular-shaped stiffening element affixed to the one or two ends of the tubular element, or to the middle portion of the tubular element. The tubular element may also include stiffening element with other configurations affixed to side wall of the tubular element. The varying shaped stiffening element is preferably embedded in the tubular element, but also can be attached to the inner or outer surface of the tubular element.

In a further preferred embodiment, the tubular element is made from a shape memory material.

Related objects and advantages of the present invention will be apparent from the following description.

BRIEF DESCRIPTION OF THE DRAWINGS

The foregoing and other objects of this invention, the various features thereof, as well as the invention itself, may be more fully understood from the following description, when read together with the accompanying drawings, in which.

DESCRIPTION OF THE PREFERRED EMBODIMENTS

The nasal breathing assist devices according to the various aspects of the invention are shown in FIGS. 1 through 10. These devices overcome the deficiencies in the currently available devices. The illustrated devices are small, inconspicuous in use, and require no special attachments or fittings. The devices are worn inside the nose, so that the nasal passages are kept open from the inside, rather than by external means. This allows the devices to maintain airways in noses where anatomical abnormalities diminish the effectiveness of externally applied strips. The devices can be used alone, or in conjunction with decongestant and antihistamines powders, tablets or liquid medications, other snore-reducing aids, such as pillows, or medicated nasal sprays.

Figure 1:
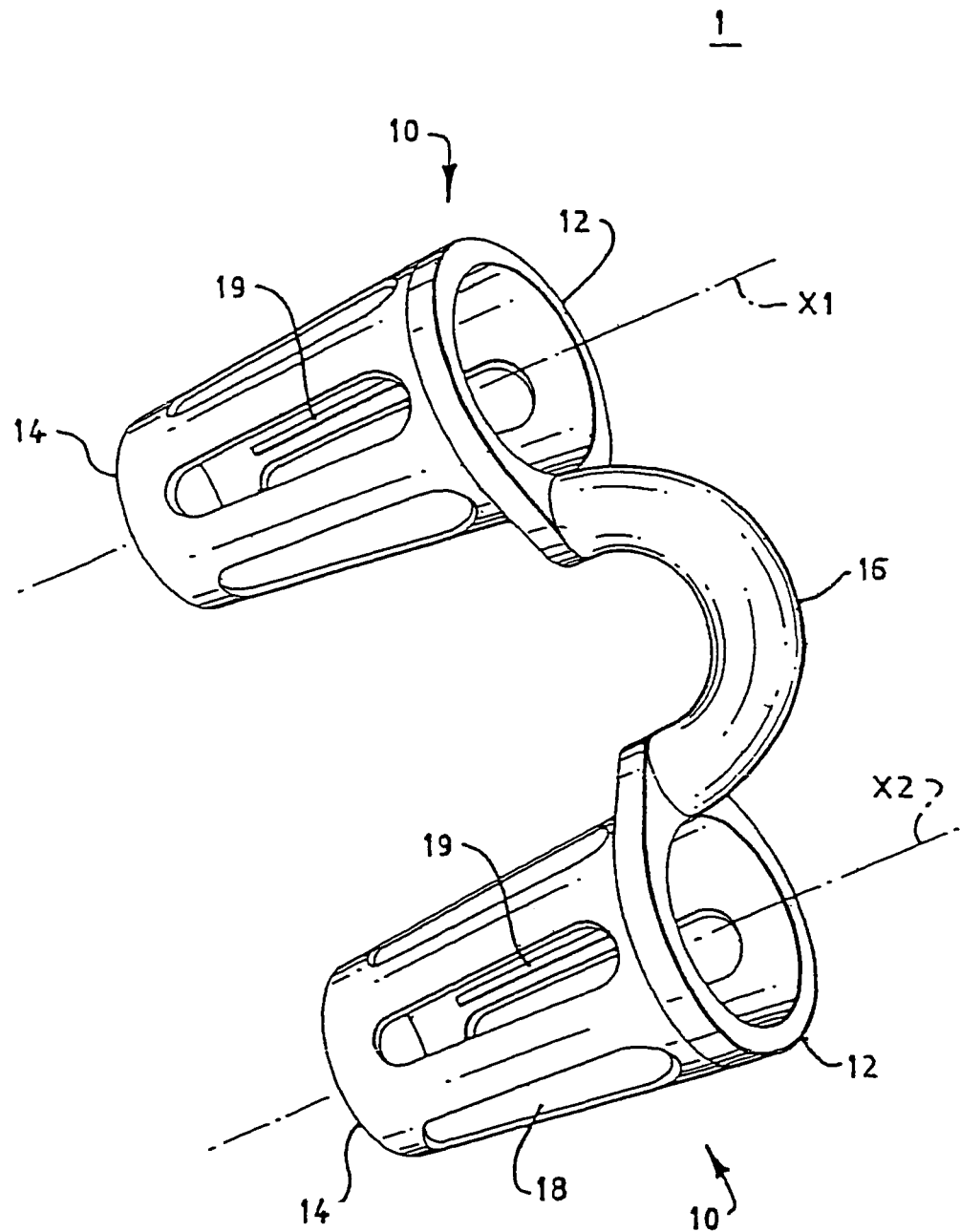
FIG. 1 is a perspective view of one embodiment of the present invention.

In the embodiment shown in FIG. 1, the nasal breathing assist device 1 comprises generally a pair of open ended tubular elements 10 connected together by a coupler element 16.

The tubular elements 10 are generally circular in cross section and extend a distance along tube axes X1 and X2 from first ends 12 to second ends 14. Preferably the tubular elements taper linearly from a relatively large diameter cross section along the tube axes X1 and X2 to a relatively smaller diameter cross section from the first end 12 to the second end 14. The taper may be other than linear, for example, contoured to correspond generally to the taper inside the user's nostrils. First ends 12 also connect to the coupler element 16. In the illustrated form, the tubular elements 10 are conic-frustums, but other shapes may be used. For example, instead of circular cross sections, the tubular elements could have elliptical or other shaped cross sections. Further, instead of the inner diameter tapering monotonically from the large end to the small end, it could decrease initially, become larger, then decrease again.

The tubular elements 10 may also include at least one passageway 18 extending through the walls of the tubular elements transverse to the tube axes X1 and X2. The passageways 18 may be circular, elliptical, or elongated at least in part in the direction of the tube axes. Alternately, the passageways can be elongated in a direction extending circumferentially around the tube axes.

The coupler element 16 is a resilient, nominally curved strut which maintains the tubular elements spaced apart, with axes X1 and X2 in a substantially parallel relationship, and in substantially a common plane. The coupler element may be made of resilient, semi-rigid, or rigid material.

Grooves 19 inside of tubular elements are an additional feature which may be used to receive medication (nasal cream) before inserting in nasal passage so as not to irritate the skin inside the nasal passage, this allows the medication to be effective without contacting the nasal passage.

Figure 2:
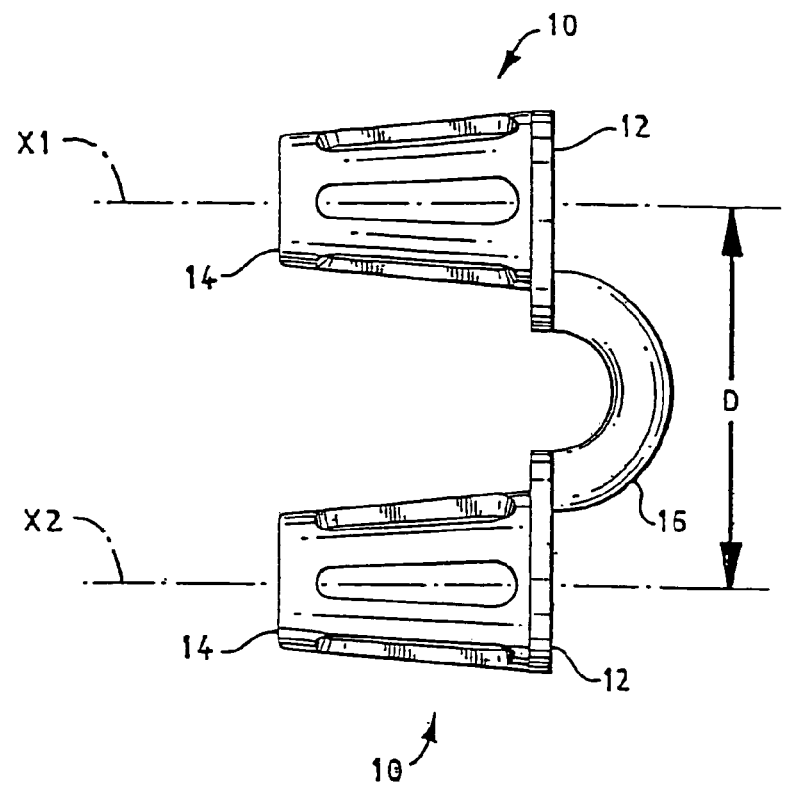
FIG. 2 shows a side view of the embodiment shown in FIG. 1.
Figure 3A:
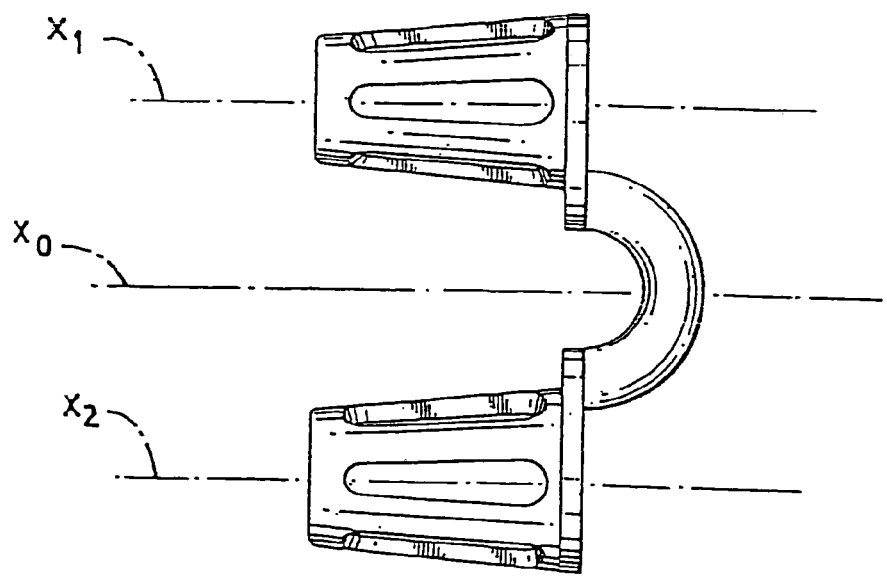
FIG. 3A shows a side view of an alternate embodiment of the invention.
Figure 3B:
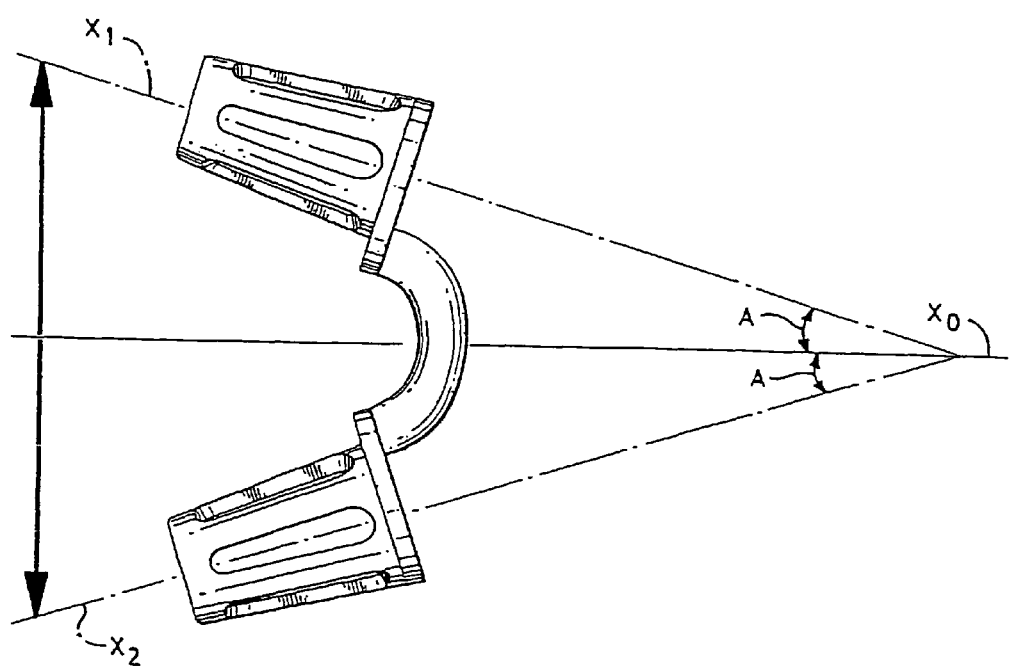
FIG. 3B shows a side view of the embodiment of FIG. 3A rotated about an axis.

As shown in FIG. 2, coupler element 16 maintains a nominal distance D between the tubular elements 10 that generally corresponds to the distance between the user's nostrils. In this embodiment, the coupler element extends in a plane that is essentially parallel to tube axes X1 and X2. As shown in FIGS. 3A and 3B, the resistance of coupler element 16 permits the axes X1 and X2 to be offset from an axis $X_0$ by angle A. Angle A can be as much as 15° or greater. Furthermore, in this embodiment, coupler element 16 permits relative flexing motion of the device about an axis, substantially perpendicular to the tube axes X1 and X2.

Figure 4A:
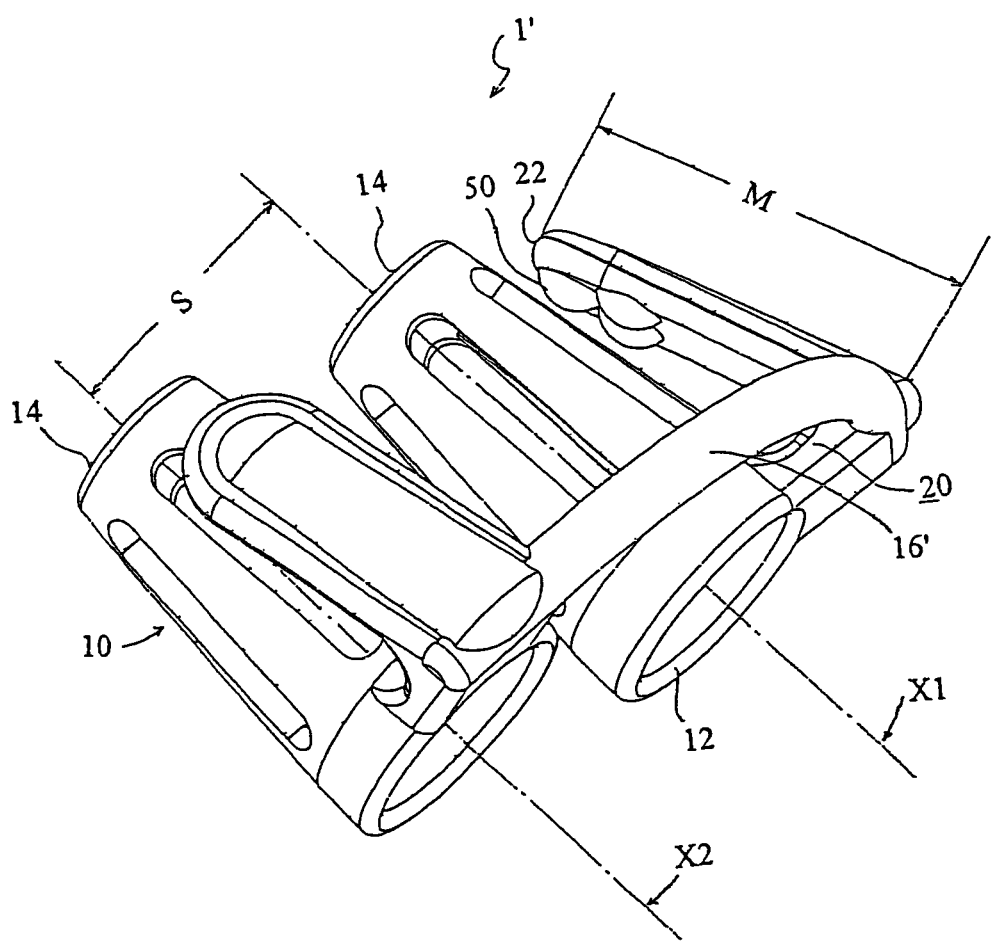
FIG. 4A is a perspective view of an alternate embodiment of the invention.

In a preferred embodiment shown in FIG. 4A, device 1' has coupler element 16' which extends between first ends 12. The central axis of coupler element 16' lies in a plane that is substantially perpendicular to the tube axes X1 and X2. In this embodiment, coupler element 16' permits relative flexing motion of device 1' so that axes X1 and X2 remain substantially parallel, but separation S of those axes varies to accommodate spacing of the nostrils.

Radially extending tab supports 20 extend from first ends 12 and connect to coupler element 16. Tabs 22 extend from tab supports 20 a distance M in the direction of the central axis to distal ends of the tabs. Tabs 22 are preferably made of non-resiliently deformable materials, for example, metal including copper, aluminum, and etc. The tab supports 20 may be made of the same or different materials as that used for the tabs 22. In use, tabs 22 remain outside the user's nostrils, and, acting as clips, help secure the device in the nostrils. The tabs 22 also function as stops which prevent the device from being wholly inserted into a user's nostril.

Figure 4B:
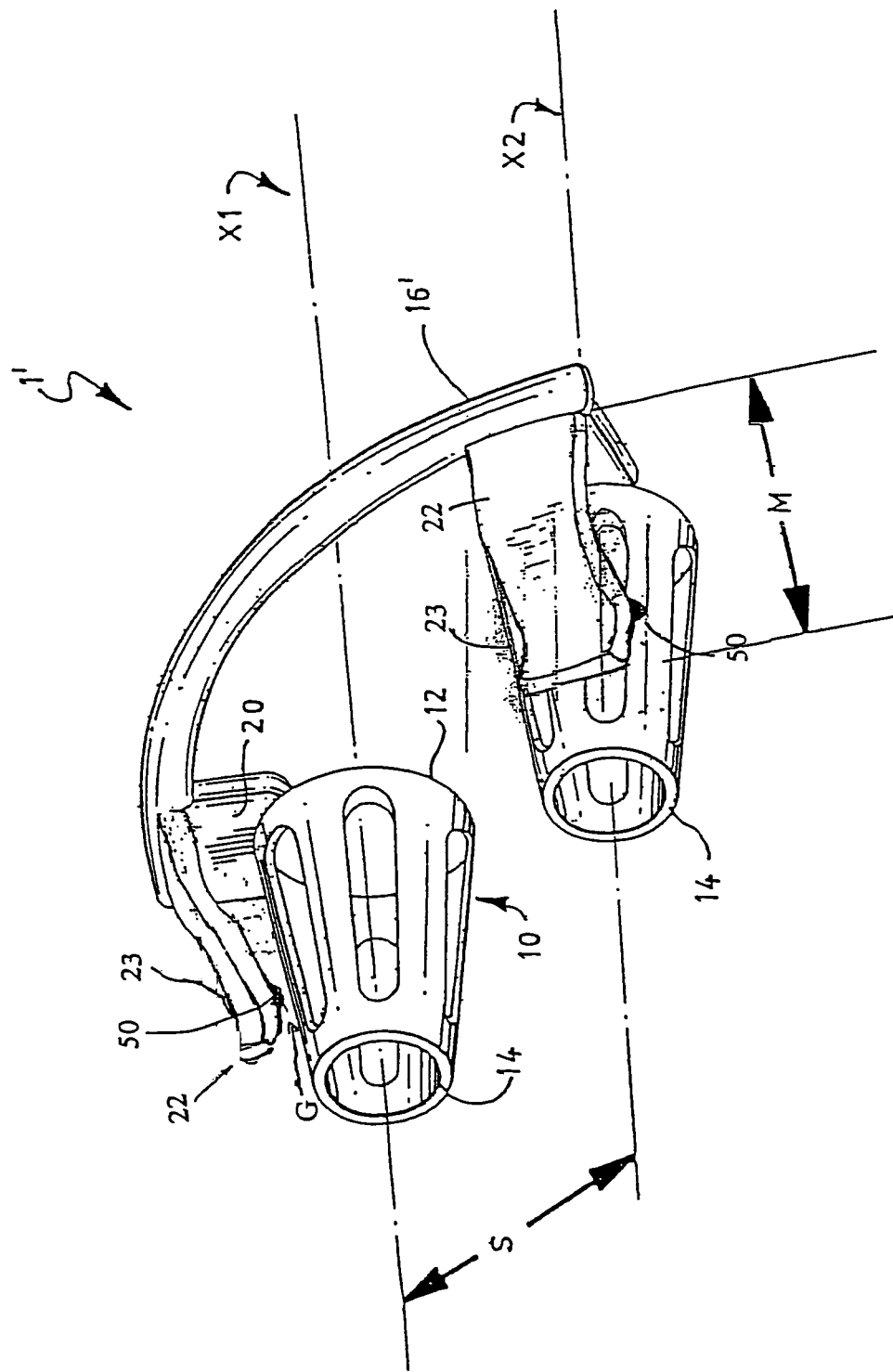
FIG. 4B is a perspective view of another alternate embodiment of the invention.

In another preferred embodiment, as shown in FIG. 4B, the tabs 22 are substantially S-shaped, and include a distal curved portion 23 distal from the first end 12. The distal curved portion 23 defines a relatively small gap G with an outer surface of the tubular element. The tabs 22 are constructed such that the small gap G is adapted to receive a lateral wall of a user's nose, and the tabs 22 are adapted to clip on the lateral wall of the user's nose. In one preferred embodiment, the tab 22 includes at least one relatively small protrusion 50 extending from the distal curved portion 23 toward the tubular element 10, as best shown in FIG. 4B and FIG. 5B. Alternatively, the relatively small protrusion 50 may extend from the outer surface of the tubular element 10 toward the distal curved portion 23 of the tab 22. In another alternate embodiment, the tab 22 includes protrusions 50 extending from the distal curved portion 23 toward the tubular element 10, and the tubular element 10 also includes protrusions opposing to the protrusions of the tab 22. In the embodiment shown in FIG. 4A, the protrusions 50 extend from a distal end of the tab 22 toward the tubular element 10. The small protrusion helps to secure the device in the user's nostrils.

Figure 5A:
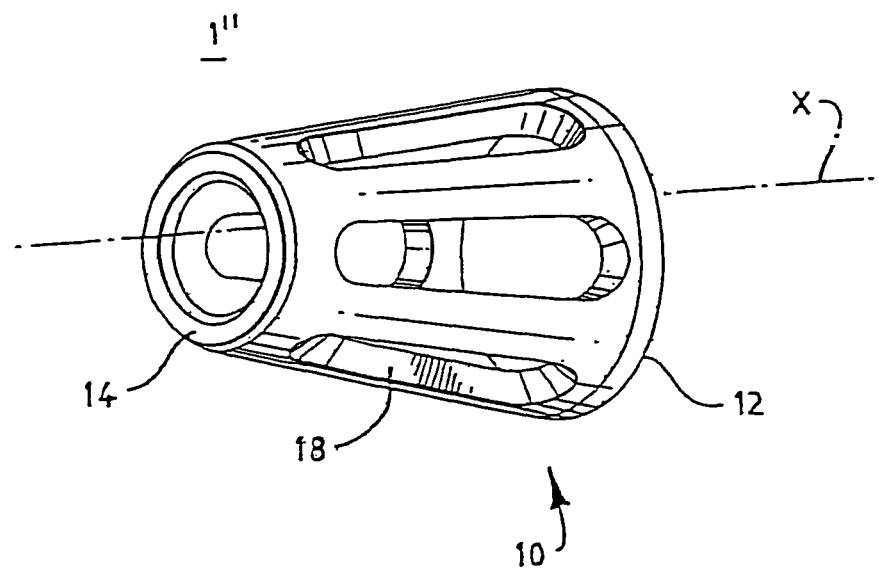
FIG. 5A is a perspective view of an alternate embodiment of the invention.
Figure 5B:
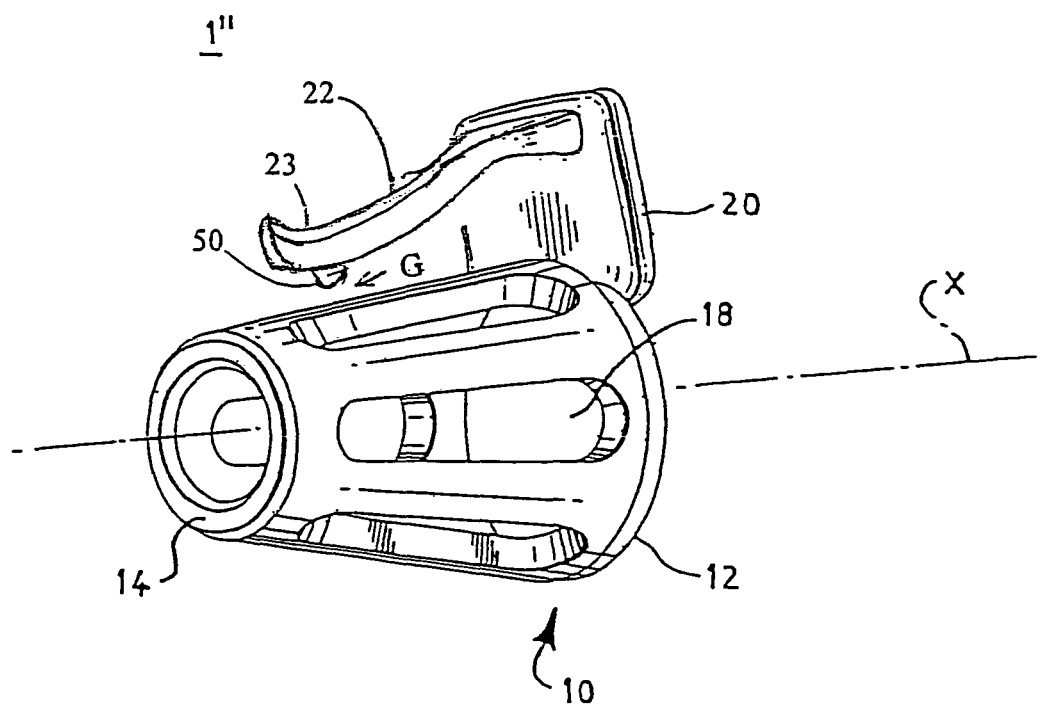
FIG. 5B is a perspective view of yet another embodiment of the invention.

FIGS. 5A-5E show other embodiments of nasal breathing assist devices. In FIG. 5A, device 1" has a tubular element 10 extending along a tube axis X between a relatively large diameter first end 12 and tapering toward a relatively smaller diameter second end 14. As previously described, tubular element 10 may have passageways 18 extending through the walls of the tubular elements transverse to tube axis X.

Figure 5C:
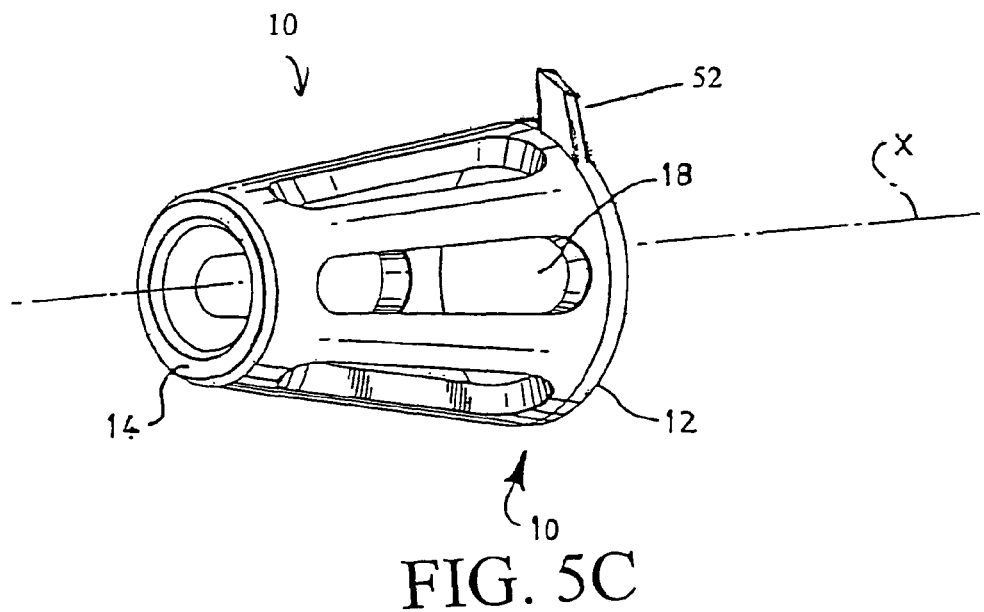
FIG. 5C is a perspective view of another embodiment of the invention.
Figure 5D:
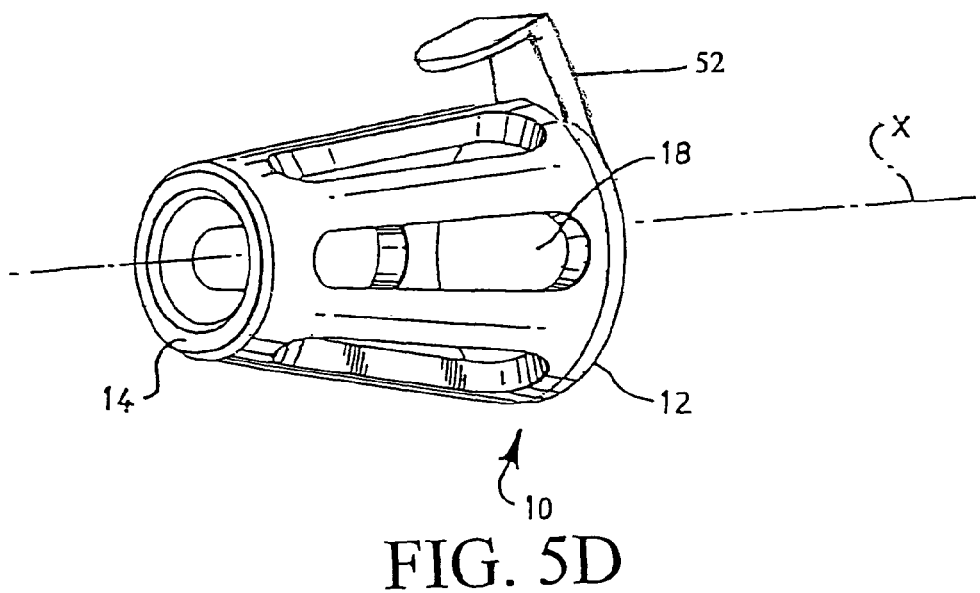
FIG. 5D is a perspective view of another embodiment of the invention.
Figure 5E:
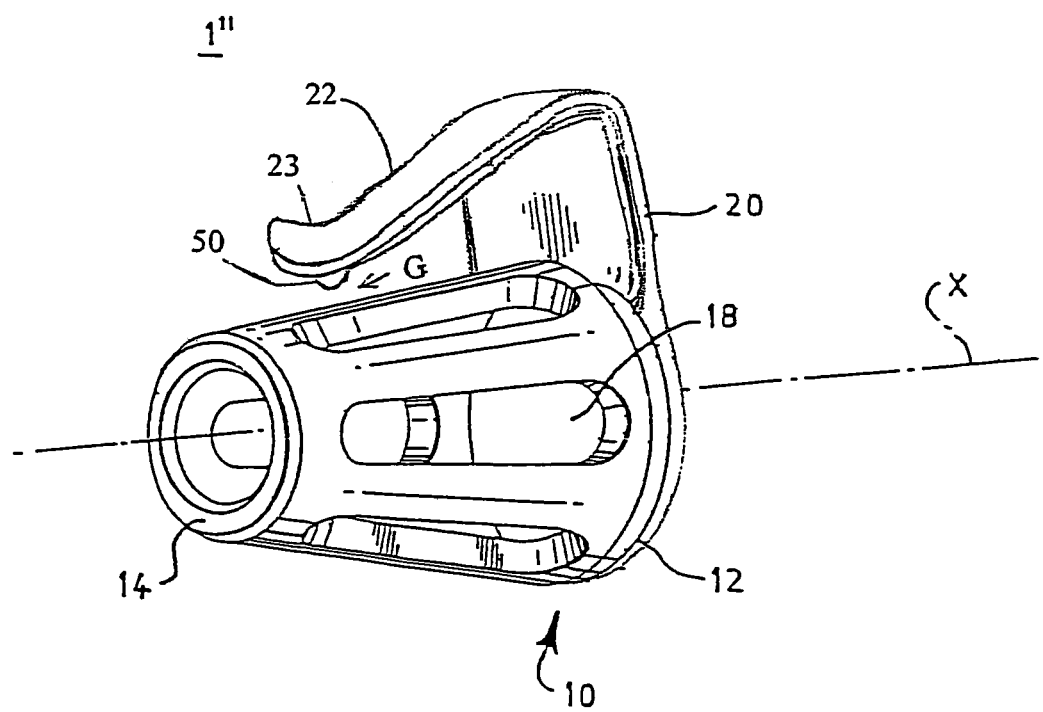
FIG. 5E is a perspective view of another embodiment of the invention.

As shown in the embodiment in FIG. 5B, radially extending tab support 20 extends from first end 12. The substantially S-shaped non-resilient tab 22 extends from tab support 20 a distance M in the direction of axis X toward second end 14. FIG. 5C illustrates another preferred embodiment, in which the device includes a stop member 52 extending radially and outwardly from the first end 12 of the tubular element to a distal end. The stop member 52 is adapted to engage with an open end of a user's nostril to prevent the device from being wholly inserted into the nostril when the device is in use. In an alternate embodiment, as shown in FIG. 5D, the stop member may further include a protrusion extending from the distal end of the stop member toward the second 14 of the tubular element 10. In another alternate embodiment, as shown in FIG. 5E, the substantially S-shaped non-resilient tab 22, the tab support 20, and the tubular element 10 are integrally constructed. In use, the protrusion remains outside the user's nostril, and, acting as a clip, helps secure the device in the nostril. Device 1" of FIGS. 5A-5E may be used singly or as a pair. The stop member 52 may also be employed in the embodiments having a pair of tubular elements connected by a coupler element.

Figure 10A:
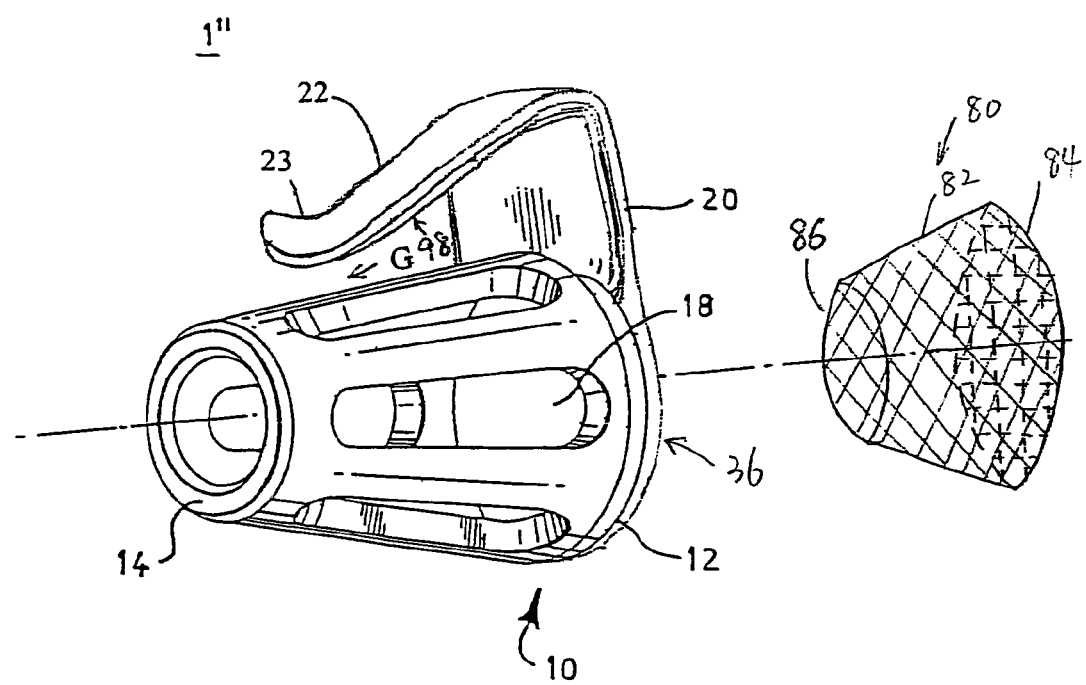
FIG. 10A shows a schematic view of a filter in accordance with one preferred embodiment of the present invention.
Figure 10B:
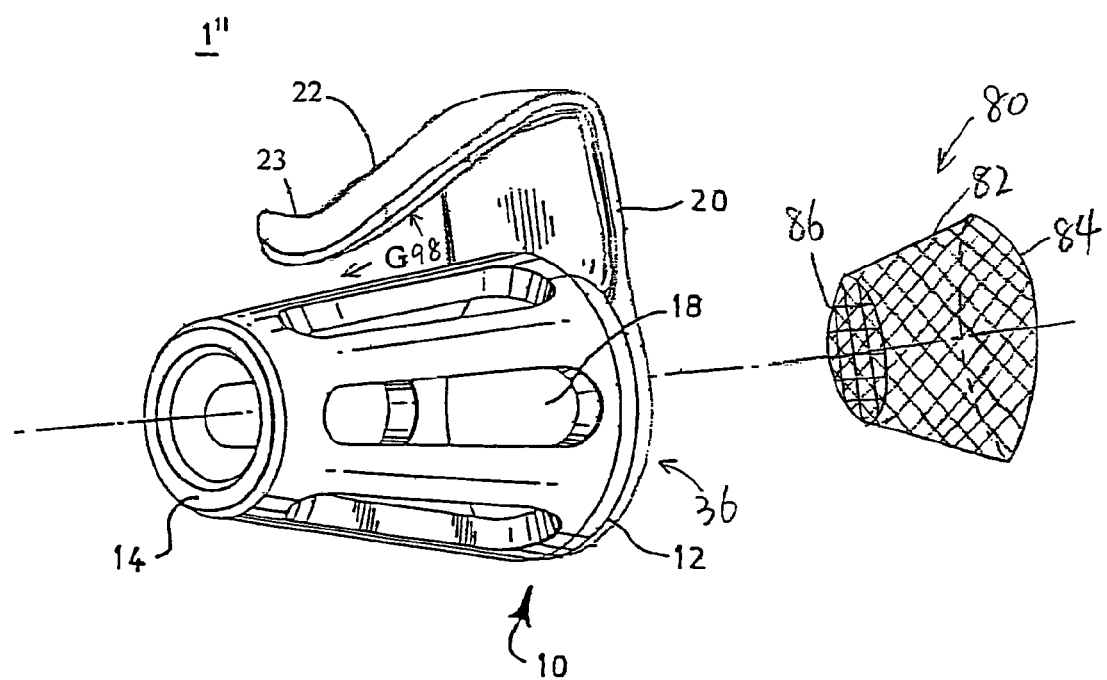
FIG. 10B shows a schematic view of a filter in accordance with another preferred embodiment of the present invention.

In another preferred embodiment, the tab 22 has an inner surface, which faces the tubular element and is at least partially coated with adhesive 98, as shown in FIGS. 10A and 10B. The tab 22 is also preferably non-resiliently deformable. In use, after the device is inserted into a user's nostrils and the tab 22 is pressed against the outer surface the user's nose, the tab 22 keeps in contact with the outer surface of the user's nose. The adhesive coating increases the friction between the tab 22 and the outer surface of the user's nose, and make the tab to stick to the outer surface of the user's nose, thus increasing the stability of the device within the user's nose. The adhesive coating of the inner surface of the tab helps to maintain the device within a user's nose, preventing the device from being knocked off during sleep, sports, or other activities.

Figure 6:
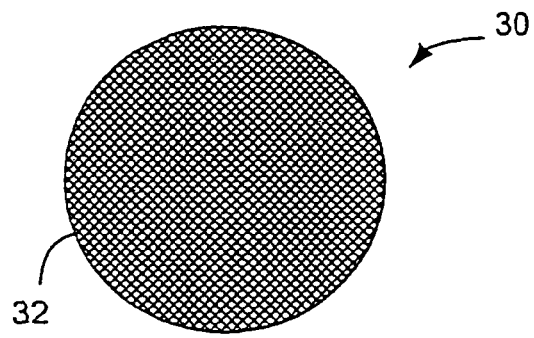
FIG. 6 shows a schematic view of a filter in accordance with one embodiment of the present invention.

FIG. 6 shows a filter 30 which may be used with the nasal breathing assist device. The filter 30 includes a filter medium, preferably a paper, a metal or plastic mesh coated with absorbent materials, spanning a frame 32. The frame 32 is preferably contoured to fit in an open-faced inner channel 36 defined in the tubular element 10. In a preferred embodiment, the tubular element 10 includes at least one relatively small protrusion 38 extending radially from an inner surface of the inner channel 36. The frame 32 of the filter 30 is adapted to snap-fit over the protrusion 38 into the inner channel 36 and is retained by the protrusion 38, thereby the filter 30 cannot slip out of the tubular element 10 when the nasal breathing assist device is in use.

Figure 7:
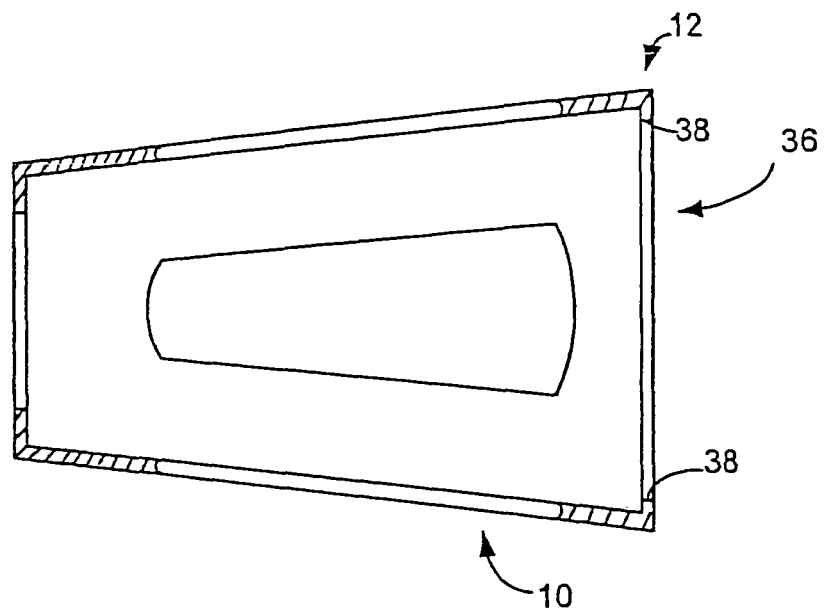
FIG. 7 shows a cross-sectional view of an alternate embodiment of the invention.
Figure 8:
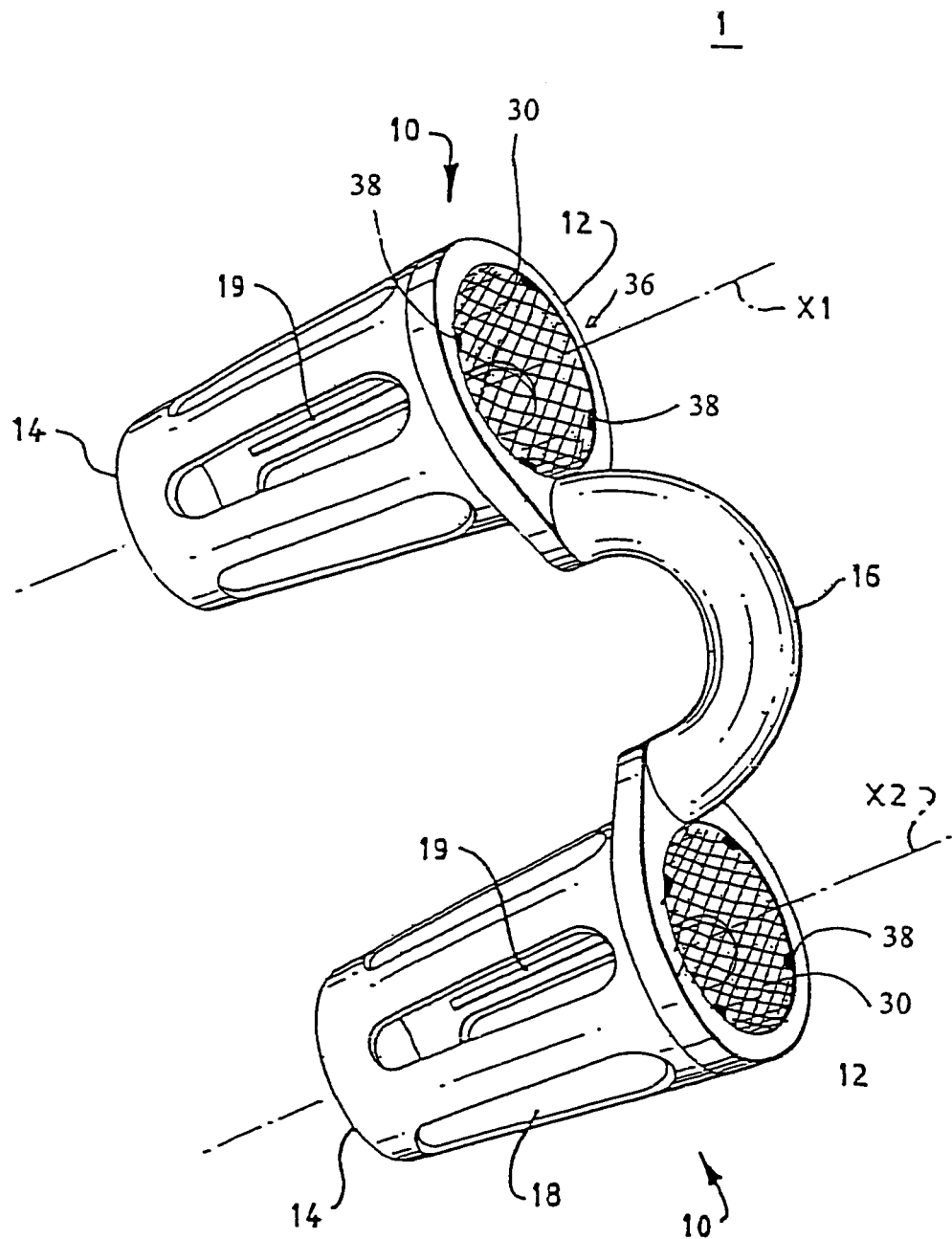
FIG. 8 shows the filter of FIG. 6 together with the nasal breathing assist device.

FIG. 7 illustrates a cross-sectional view of one tubular element 10 in accordance with one preferred embodiment of the invention. As shown in FIG. 7, the protrusion 38 extends throughout an inner circumference at the first end 12 (the end with a relatively large diameter) of the inner channel 36. The filter 30 is snap-plugged into the channel 36 from the first end of the channel 36, and because the diameter of the channel 36 tapers from the first end to the second end, the filter can be secured by the inner surface of the channel 36 and the protrusion 38. The protrusion 38 is relatively small, so that the filter 36 can be easily removed and replaced. FIG. 8 shows a schematic view of the filters 30 together with a nasal breathing assist device. Each tubular element 10 includes relatively small protrusions 38 securing the filter 30 at the first end of the tubular element 10. The filter 30 is preferably positioned at one of the two ends of the tubular element 10, so that the filter 30 can be easily removed and replaced, but the filter 30 also can be positioned at a place between the two ends and secured by protrusions extending radially adjacent that place.

Figure 9:
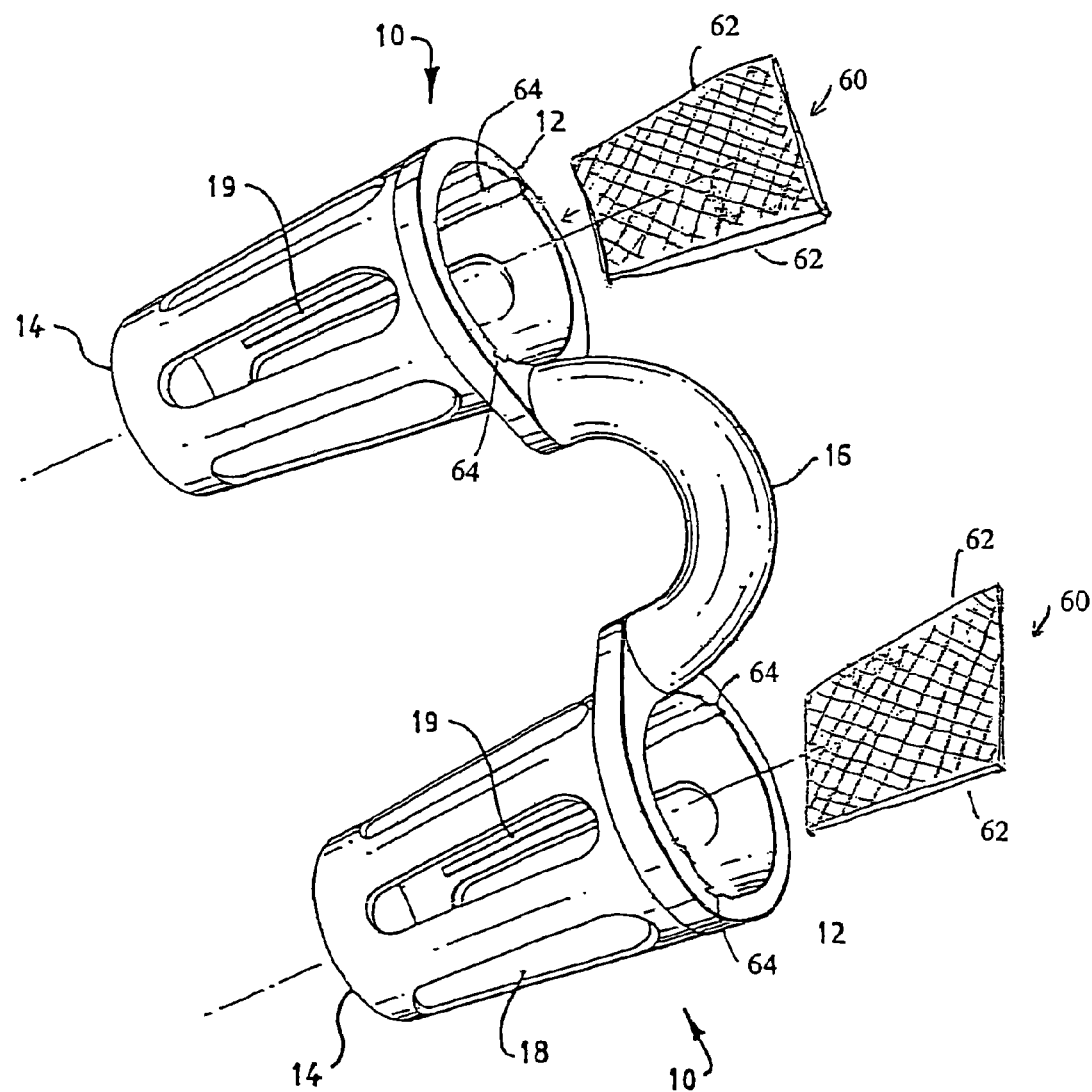
FIG. 9 shows another preferred embodiment of the invention.

FIG. 9 illustrates another preferred embodiment of the present invention. As shown in FIG. 9, the device further includes at least one removable medication carrier 60 which may include a medium adapted to bear a therapeutic agent. The removable carrier 60 preferably includes a frame tapering from a first end to a second end. The frame includes two opposite edges 62. The tubular element 10 further defines two opposing channels 64 on an inner surface of the tubular element 10. The two opposing channels 64 extend substantially in the same direction as the central axis and are adapted to receive the two opposite edges 62 of said removable carrier 60. The frame of the removable medication carrier 60 may be constructed with other shapes, and the tubular element may define corresponding channels or other mechanism for receiving the frame of the carrier 60. The therapeutic agent may be medications, for example, antibiotics, for treating chronic sinusitis or other nasal diseases.

In alternative embodiments, as illustrated in FIGS. 10A and 10B, the filter is a liner filter (as denoted by number 80 in FIGS. 10A and 10B) including a conic-shaped liner portion 82 extending between two ends 84 and 86. One end has a relatively large diameter and the other end has a relatively small diameter. In the embodiment shown in FIG. 10A, the relatively large end 84 is a closed end having a filter medium spanning the circumference of the end of the liner portion, and the other end 86 is an opened end. In an alternative form, as shown in FIG. 10B, the filter medium is attached to the relatively small end 86, and the relative large end is an open-faced end.

The liner portion 82, preferably but not necessarily, is constructed by the filter medium. The filter 80 preferably but not necessarily is made from a unitary sheet of a filter medium by a molding process. The filter 80 is sized to fit in the open-faced inner channel 36 defined in the tubular element 10. The tubular element 10 may include at least one relatively small protrusion extending radially from an inner surface of the inner channel 36 at the relatively large end of the tubular element for preventing the liner filter 80 from slipping out of the channel 36 of the tubular element 10. In use, the liner filter 80 is inserted into and retained in the inner channel 36 of the tubular element 10. The liner filter 80 can be easily removed from the inner channel 36, and can be replaced or cleaned.

The filter medium is constructed to filter pollen, dust, mold, and/or other particles that may cause allergic reactions or other diseases or discomfort. In an alternative form, the filter medium is preferably made from a material that can be coated with medications, particularly, medications for treating nasal diseases. Exemplary medications include decongestants, antihistamine, and antibiotic.

The filters as illustrated in FIGS. 6-8, the medication carriers shown in FIG. 9, and the liner filters as shown in FIGS. 10A and 10B can be used with nasal breathing assist devices, which have one tubular element or have a pair of tubular elements connected by a strut, as described in the previous embodiments. The nasal breathing assist devices can be disposable or reusable. The reusable devices can be easily cleaned by rinsing with soap and water.

Figure 11A:
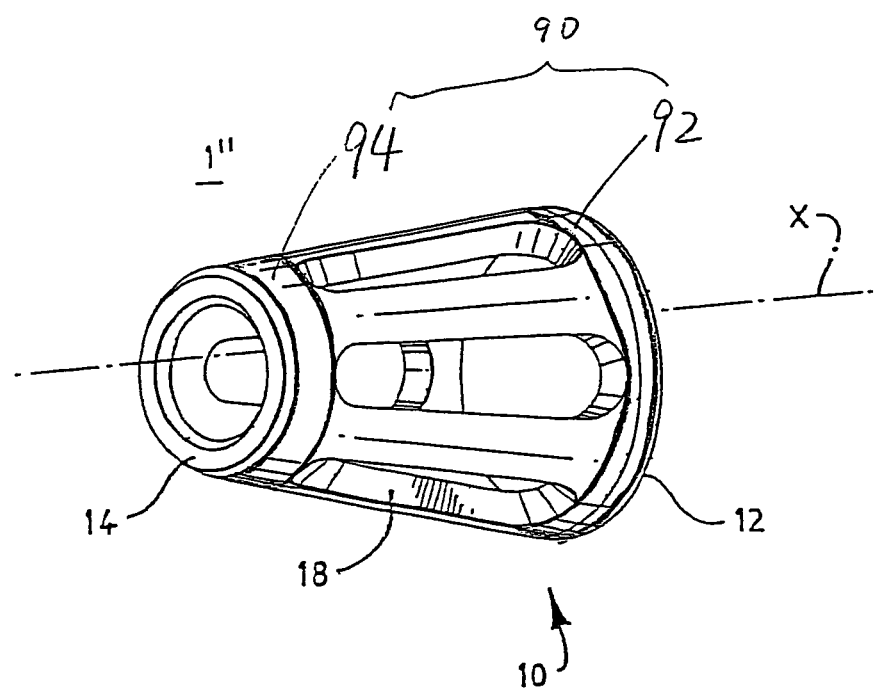
FIG. 11A shows a perspective view of another preferred embodiment of the present invention.

The device can be made of rigid, semi-resilient, or resilient materials. In one preferred embodiment, the tubular element 10 includes at least one stiffening element 90 embedded in or attached to the tubular element. The stiffening element 90 is preferably made from a material with a higher hardness value than the rest part of the tubular element 10. In one preferred form, as shown in FIG. 11A, the stiffening element 90 includes two rigid rings 92, 94 extending about the central axis of the tubular element 10 and embedded in the conic wall of the tubular element 10, one of the two rings, for example, the ring 92, preferably embedded at or near the relatively large end of the tubular element 10, and the other (ring 94) embedded at or near the relatively small end of the tubular element 10. The device could include more than two stiffening rings, and/or other shape stiffening parts embedded in the conic wall of the tubular element 10. Alternatively, the stiffening element 90 also can be attached to the inner surface or outer surface of the tubular element 10. The stiffening element prevents the tubular element 10 from collapse when under pressure and maintain opening of the nasal passage in severe cases, for example, pathologic nasal valve collapse, septal deviation, and other types of nasal congestion or obstruction. The stiffening element also increases the resilience of the tubular element 10 and the stability of the tubular element 10 within a user's nostrils.

Figure 11B:
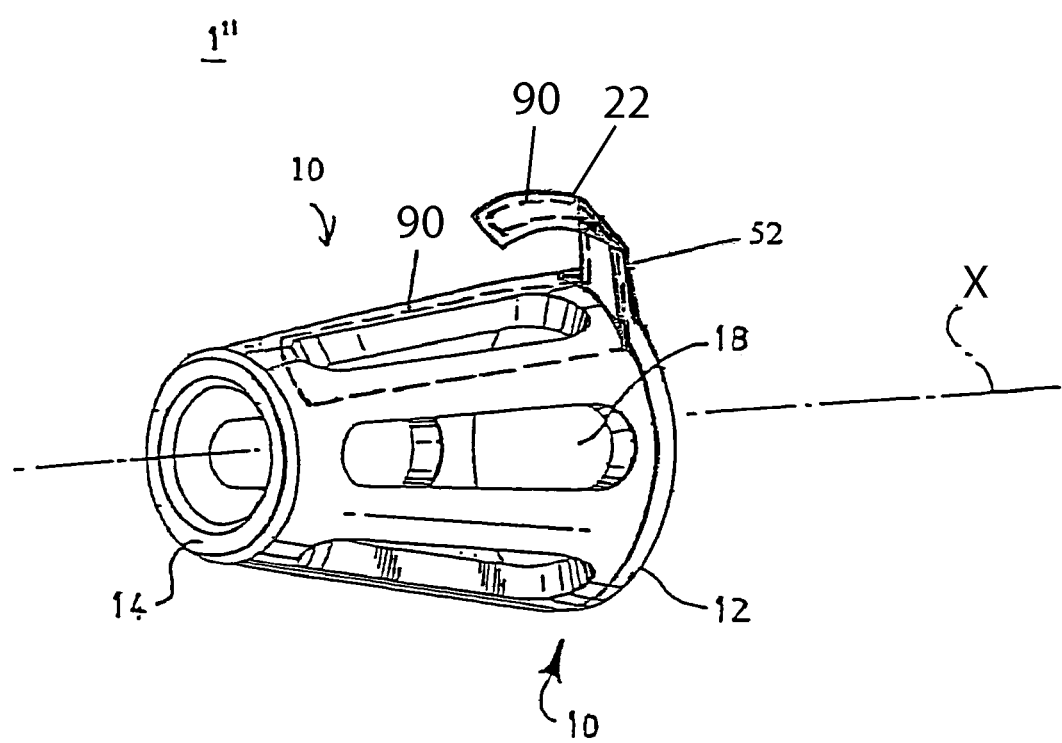
FIG. 11B shows a perspective view of another preferred embodiment of the present invention.

In another preferred embodiment, as shown in FIG. 11B, the stiffening element 90 includes an elongated wire embedded within the tubular element 10 and the tab 22.

In one preferred embodiment, part of the device is made from a non-resiliently deformable material, for example, aluminum. Preferably, the tabs 22 shown in FIGS. 4A-5E are made from a non-resiliently deformable material. In another preferred embodiment, as shown in FIG. 11B, an elongated metal wire is embedded within the tubular element 10 and the tab 22. In one preferred form, the wire is non-resiliently deformable, enabling the tab 22 to be non-resiliently deformable. In another preferred form, the wire is made from a resilient material, enabling the tab 22 to be resiliently deformable. In use, after the device is inserted to a user's nostrils, the user can force the tab 22 toward the outer surface of the user's nose to allow the tab 22 to touch the outer surface of the user's nose. The tab 22 will stay in contact with the outer surface of the user's nose, thus preventing the device from slipping out of the user's nose.

In a further preferred embodiment, at least part of the device is made from a shape memory material. For example, the device may have one shape under room temperature, and after the device is inserted into the user's nostrils, where the temperature is normally higher than the room temperature, the device returns to it's original shape that fit the contour of the inside of the user's nostrils. The device may also be coated, or embedded with medications for treating nasal diseases, or other diseases, such as skin or mucous diseases.

Figure 12:
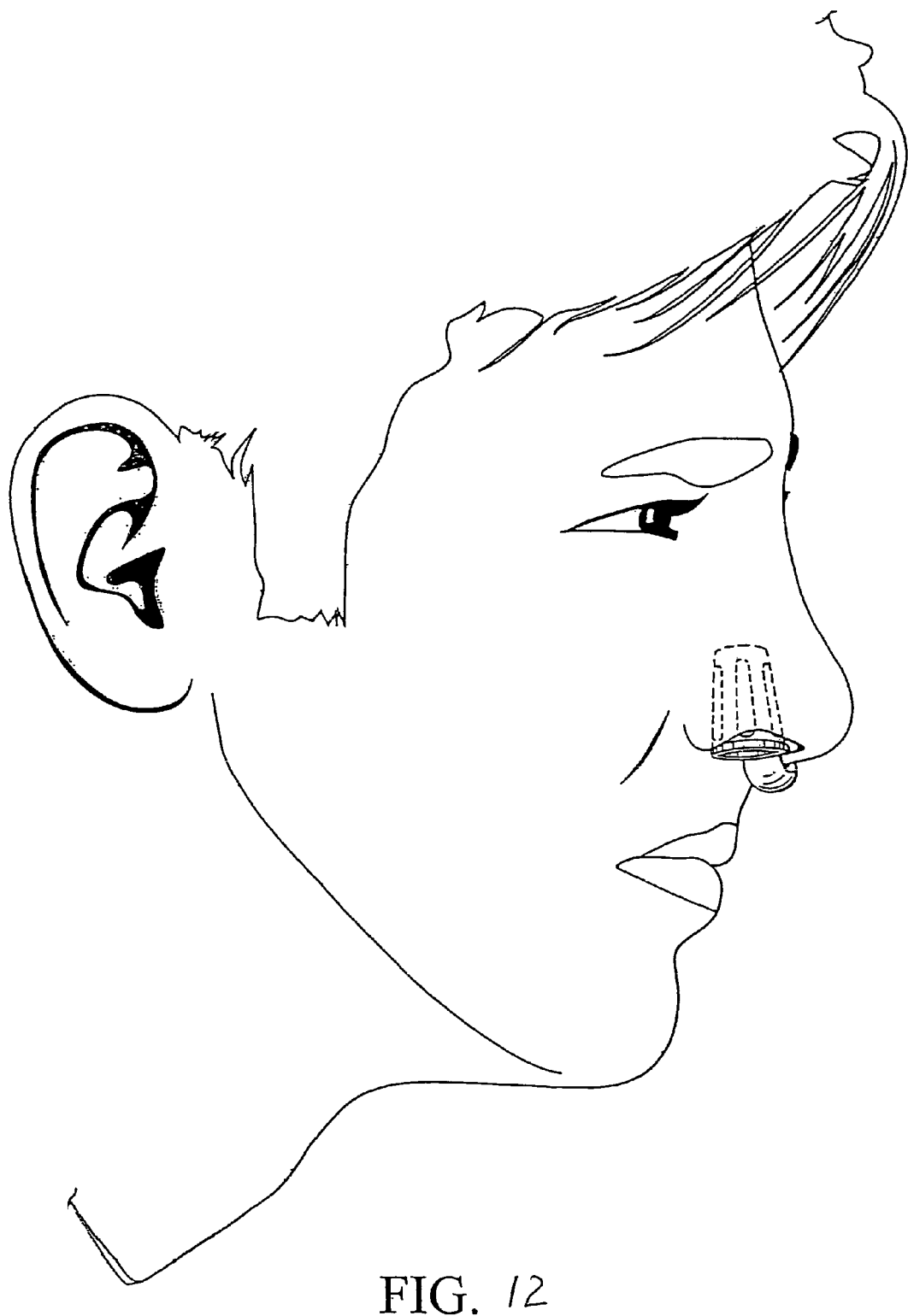
FIG. 12 is a representation of one embodiment of the invention in use.

The nasal breathing assist device is inserted in the user's nostrils, as shown in FIG. 12, usually at bedtime. The tubular elements maintain open nasal passages during sleeping, which allow the patient to obtain sufficient airflow through the nose only, rather than supplementing the air supply through the mouth. The filters can be made to absorb or hold pollen, dust, particles in smoke and smog fumes, nicotine in tobacco smoke, obnoxious odors, and other irritating elements.

The nasal breathing assist devices can be used to aid in the administration of nasally supplied drugs and medications, either at bedtime or during the day, for example, using a medication carrier inserted in the tubular element to deliver medications through the nose. The nasal breathing assist device can also be used with other conventional devices to supply drugs and medications, for example, the user can insert the device into the nose, and spray a nasal medication, or moisture mist agent into the nose. The passageways in the device act to help circulate the medication or agent within the nasal passageways by keeping the nasal passages open.

The invention may be embodied on other specific form without departing from the spirit or essential characteristics thereof. The present embodiments are therefore to be considered illustrative and not restrictive, the scope of the invention being dictated by the appended claims rather than by the foregoing description, and all changes which come within the meaning and range of equivalency of the claims are therefore intended to be embraced therein.

What claimed is:

1. A nasal breathing assist device comprising:
an open-ended tubular element extending along a central tube axis between a relatively large first end and a relatively smaller second end, a tab attached to and extending from the first end of the tubular element at least partially in a direction transverse to the central tube axis and outside of the tubular element, and
at least one stiffening element that
   (i) extends from the tubular element to the tab,
   (ii) is embedded in the tubular element and in the tab, and
   (iii) comprises a material that has a higher hardness value than that in which it is embedded.

2. The device according to claim 1, wherein the tab comprises a proximal tab end attached to the first end of the tubular element to a free distal tab end that is closer to the second end of the tubular element than is the proximal tab end.

3. The device according to claim 2, wherein said tab has an inner surface facing an outer surface of said tubular element, wherein said inner surface of said tab is at least partially coated with adhesive.

4. The device according to claim 2, wherein said tab is substantially S-shaped, and comprises a distal curved portion adjacent said distal end, said distal curved portion defining a gap with an outer surface of said tubular element, said gap being sized and shaped to receive a lateral wall of a user's nose, and said tab being sized and shaped to clip on the lateral wall of the user's nose.

5. The device according to claim 2, wherein said tab is made from a non-resiliently deformable material.

6. The device according to claim 1, wherein said tubular element is made from a shape memory material.

7. The device according to claim 1, wherein said at least one stiffening element is attached to a lateral wall of said tubular element.

8. The device according to claim 1, wherein said at least one stiffening element is embedded within a lateral wall of said tubular element.

9. The device of claim 1, wherein the tubular element defines at least one groove along a lateral wall of the tubular element, the groove being defined on a side of the lateral wall that faces the tubular element interior.

10. The device of claim 9, wherein the groove does not penetrate the tubular element lateral wall.

11. The device of claim 9, wherein the grooved tubular element further defines at least one aperture through the lateral wall.

12. The device of claim 11, wherein the groove does not penetrate the tubular element lateral wall.

13. The device of claim 1, wherein the tubular element is conic-frustum shaped.

14. The device of claim 1, wherein at least one stiffening element comprises metal, the tab comprises plastic, and the metal is embedded in the plastic.

15. The device of claim 1, wherein the tab is substantially C-shaped.

16. The device of claim 1, wherein the tubular element and the tab are formed from a first material.

* * * * *